(12) United States Patent
Dunfield et al.

(10) Patent No.: US 7,141,386 B2
(45) Date of Patent: Nov. 28, 2006

(54) CELL CULTURE DEVICE

(75) Inventors: John Stephen Dunfield, Corvallis, OR (US); Ronni J. Yenchik, Blodgett, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 644 days.

(21) Appl. No.: 10/285,800

(22) Filed: Oct. 31, 2002

(65) Prior Publication Data
US 2004/0086844 A1 May 6, 2004

(51) Int. Cl.
*C12Q 1/24* (2006.01)

(52) U.S. Cl. ............ 435/30; 435/284.1; 435/286; 435/287.3; 435/288; 422/68.1; 347/2; 347/85; 347/96; 427/2.11

(58) Field of Classification Search ............ None
See application file for complete search history.

(56) References Cited

U.S. PATENT DOCUMENTS

| | | | |
|---|---|---|---|
| 5,424,209 A | 6/1995 | Kearney | ............ 435/284 |
| 5,451,524 A | 9/1995 | Coble et al. | |
| 5,593,814 A | 1/1997 | Matsuda et al. | ............ 430/320 |
| 5,641,644 A * | 6/1997 | Klebe | ............ 435/30 |
| 5,763,261 A | 6/1998 | Gruenberg | ............ 435/286.5 |
| 5,882,918 A | 3/1999 | Goffe | ............ 435/286.6 |
| 5,900,361 A | 5/1999 | Klebe | ............ 435/30 |
| 6,096,532 A | 8/2000 | Armstrong et al. | ...... 435/286.5 |
| 6,197,575 B1 | 3/2001 | Griffith et al. | ............ 435/288.4 |
| 6,228,635 B1 | 5/2001 | Armstrong et al. | |
| 6,238,908 B1 | 5/2001 | Armstrong et al. | ...... 435/286.5 |
| 6,277,642 B1 | 8/2001 | Mentzen et al. | |
| 6,403,369 B1 | 6/2002 | Wood | ............ 435/304.1 |
| 2002/0177221 A1* | 11/2002 | Nishiguchi et al. | ...... 435/287.2 |

OTHER PUBLICATIONS

EP Search Report.

* cited by examiner

*Primary Examiner*—David Redding (57) ABSTRACT

A culture device for cellular media including a biomedia growth chamber defining a closed environment and an electronically controllable jetting device in communication with a source of material supporting biological function. The jetting device emits the material into the biomedia growth chamber.

78 Claims, 3 Drawing Sheets

```
110
EXPOSE CULTURE DEVICE TO ENVIRONMENT
     │
     ▼
120
ADMIT QUANTITIES OF ENVIRONMENTAL MATERIAL
INTO BIOMEDIA CULTURE CHAMBER
     │
     ▼
130
MEASURE RESPONSE EXHIBITED BY
CELLULAR MATERIAL
```

FIG. 6

```
210
MAINTAIN BIOFUNCTIONAL MATERIAL IN
MICROCULTURE DEVICE
     │
     ▼
220
INTRODUCE MATERIAL AFFECTING BIOFUNCTIONAL
MATERIAL FROM JETTING DEVICE
     │
     ▼
230
REMOVE BYPRODUCT OF METABOLIC
FUNCTION FROM MICROCULTURE DEVICE
     │
     ▼
240
ISOLATE BIOLOGICALLY DERIVED COMPOUND
```

FIG. 7

CELL CULTURE DEVICE

FIELD OF THE INVENTION

The present invention is directed to a cell culture device and to microdevices capable of utilizing biological cytosensors. The present invention is also directed to methods for keeping various cell lines viable, particularly in small portable microfluidic packages.

BACKGROUND OF THE INVENTION

Various devices and methodologies have been suggested for the controlled culture of cells and cell lines. Such devices can facilitate controlled delivery of supportive materials, toxins, other challenge materials and the like. However, these devices each possess attributes which are subject to improvement and enhancement. Typical culture devices require the culture and maintenance of several thousand cells at minimum. It can be appreciated that an environment having several thousand or more cells can make it difficult to study or observe reactions and functions on an individual cellular or subcellular level. Thus, the need to provide cell culture devices which can sustain cell populations between 1 and approximately 10,000 is largely unmet.

SUMMARY OF THE INVENTION

The present invention is directed to a culture device which includes a storage chamber, a jetting device in communication with the storage chamber, and a biomedia growth chamber in contact with the jetting device such that the biomedia growth chamber defines a closed growth environment.

DETAILED DESCRIPTION OF EMBODIMENTS

Figure 1:
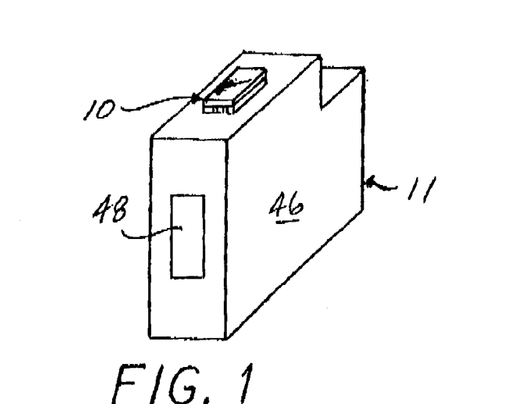
FIG. 1 is a perspective view of a cellular culture device in communication with an associated cartridge.

Disclosed herein is a culture device 10 for cellular media. Culture device 10 is shown in FIG. 1 in combination with a cartridge device 11 which is configured to carry significant quantities of various material required to sustain cellular function. It is contemplated that cellular culture device 10 can be either permanently or removably affixed to an associated cartridge 11. It is also contemplated that culture device 10 can be removably attached to a suitable cartridge such as cartridge 11 to further facilitate analysis, observation and the like.

Figure 2:
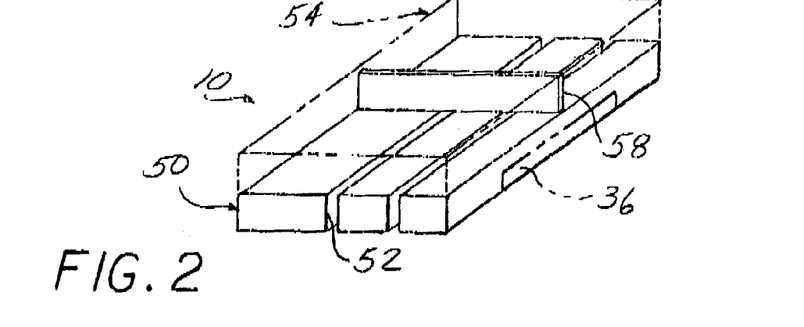
FIG. 2 is a perspective view of a culture device of FIG. 1.
Figure 3:
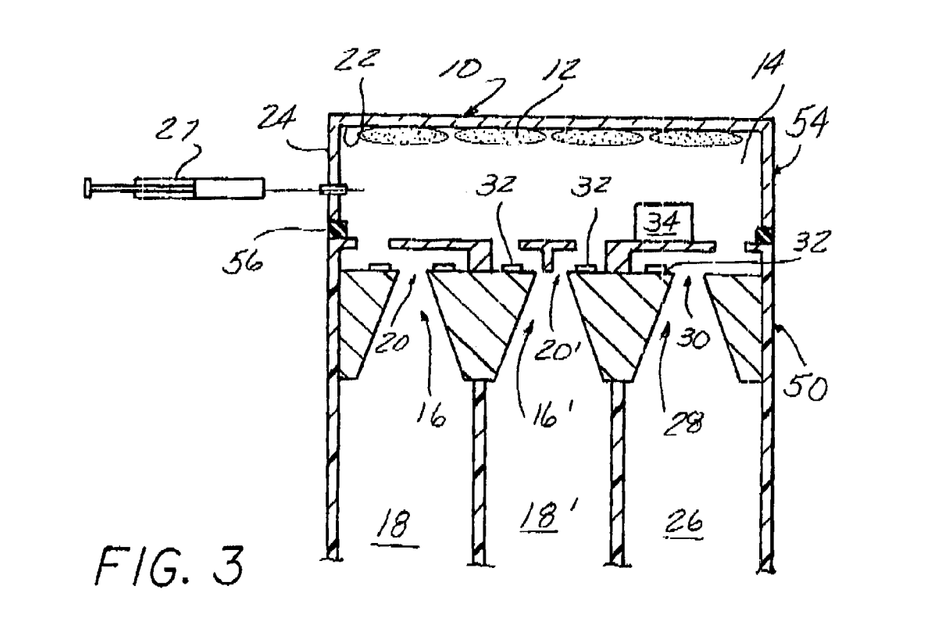
FIG. 3 is a cross-sectional view of a the cellular culture device of FIG. 2.

As seen in FIGS. 2 and 3, the culture device 10 for cellular media includes a biomedia growth chamber 14 which defines a closed environment in which cellular media can be grown, cultured and/or studied. The culture device 10 also includes an electronically controllable jetting device such as devices 16, 16' in communication with a source of material supporting biological function. The electronically controllable jetting device 16 emits material into the biomedia growth chamber 14. While culture device 10 as depicted describes two electronically controllable jetting devices 16, 16', it is contemplated that the cell culture device 10 can contain any number of electronically controllable jetting devices necessary to deliver various materials to the biomedia growth chamber as desired or required.

As used herein, the term "biomedia" is taken to mean individual cells, homogeneous colonies of cells, colonies of cells having mixed cell lineage as well as subcellular organelles, and more primitive microscopic material such as viruses, retroviruses, and the like. Examples of such subcellular organelles include, but are not limited to, mitochondria, material derived from or including the nucleus or nucleolus, and the like. Suitable biomedia will be material which can be supported in the biomedia growth chamber 14 and is capable of maintaining at least one biological function of interest for a limited interval within the biomedia growth chamber 14.

The term "cellular media" is taken to include individual intact cells as well as subcellular organelles capable of performing at least one biological function for a limited interval within the confines of the biomedia growth chamber 14. Where necessary, it may also include material such as sera and the like which acts as an associated growth or support medium for the cells. The biological function performed can include any chemical, biochemical, electrochemical or physical function of interest. Examples include but are not limited to energy transport, mitochondrial RNA replication, ATP/ADP mediated energy transport, photosynthesis, protein synthesis and the like. It is also contemplated that the "cellular media" can include more primitive biological material such as viruses, retroviruses and the like. Such biological material can be derived from any suitable source including, but not limited to, complex multicellular organisms, unicellular organisms, heterogeneous or homogeneous cellular lines, various clonal lines, and subcellular material.

The electronically controllable jetting device 16,16' employed in the culture device 10 is one which is capable of emitting quantities of an associated material capable of affecting and/or supporting biological function into the biomedia growth chamber 14 upon receipt of an appropriate control command. The associated material to be introduced through the electronically controllable jetting devices 16, 16' can be introduced from any suitable source. Examples of jetting device technology suitable for use in the culture device in the present invention include jetting devices and architecture found in ink jet devices. Such jetting devices include, but are not limited to, thermal ink jet devices, piezo-electric ink jet devices and the like.

The materials transferred through the electronically controllable jetting device 16, 16' are those which support and/or affect biological function. "Support of biological function" as this term is employed herein is taken to mean that the material is one which is necessary or desirable for promoting or maintaining the cellular media 12 contained in biomedia growth chamber 14. Broadly construed, the materials supporting and/or affecting biological function include, but are not limited to, various nutrients such as proteins and energy sources, as will as electrolytes, trace metals, and the like. Various nutrient materials can be associated with various electronically controllable jetting devices 16, 16' to alter or vary the nutrient profile introduced into the biomedia growth chamber 14. Electronically controllable jetting devices 16, 16' can also be configured to transfer other materials of interest or under study into the biomedia growth chamber. Such materials include, but are not limited to inoculants, potential toxins, and other materials which may affect function of the cellular material.

As depicted in the drawing figures, particularly FIGS. 1–3, the culture device 10 of the present invention comprises a storage reservoir 18, 18', which is in communication with an associated electronically controllable jelling device 16, 16'. It is contemplated that the storage reservoir 18, 18' will be of sufficient volume to contain material necessary for supporting biological function. As depicted in FIG. 1, it is contemplated that reservoirs are contained within cartridge 11 as a number of discrete storage chambers suitable for containing the materials to be introduced into the biomedia growth chamber 14. However, it is also contemplated that reservoirs 18, 18' can be configured to hold significantly smaller volumes depending upon the nature of the cellular media 12 contained in the biomedia growth chamber 14 and the use to which the cell culture device 10 is to be put. Thus, it is contemplated that the storage reservoirs 18, 18' can be positioned on any suitable storage substrate and may be of any size desired or required to support cellular activity for the useful life of the device 10.

The electronically controllable jetting device 16, 16' is configured within orifice outlet 20, 20' in communication with the biomedia growth chamber 14 such that materials contained in associated storage reservoirs 18, 18' can be emitted in discrete quantities. The biomedia growth chamber 14 is positioned to overlay the orifice outlet 20, 20' defined in the jetting device 16, 16'. It is contemplated that the culture device 10 will include multiple orifice outlets 20, 20' in connection with multiple electronically controllable jetting devices 16, 16'. The biomedia growth chamber 14 may overlay the multiple orifice outlets.

The biomedia growth chamber 14 can include a suitable biomedia support surface 22 which is configured to maintain and promote the growth of the cellular medium in a particular location. The biomedia support surface 22 is positioned relative to the jetting devices 16, 16' to facilitate administration of the materials supporting biological function and to facilitate observation and analysis of a given biological function of the cellular media. As depicted in FIG. 3, the biomedia support surface 22 is integral to chamber housing 54. However, the biomedia support surface 22 may be a separate structure or substructure on which the cellular media 12 can be cultured and supported.

The culture device 10 can also include suitable mechanisms for permitting controlled external access into the biomedia growth chamber 14. Such access can be necessary to accomplish functions such as introducing challenge material into the biomedia growth chamber 14 or localized regions thereof. Examples of challenge media can include, but are not limited to, various inoculation compounds or compositions which may alter or affect the biological function of the cellular media 12. The inoculation compounds may be toxins, pathogenic agents, growth factors, characterized proteins, uncharacterized proteins, environmental agents or other materials of interest. One such mechanism is inoculation septum 24, which is defined and positioned in chamber housing 54 to provide sealable access between the biomedia growth chamber 14 and environment external to the biomedia growth chamber 14. The inoculation septum 24 is configured to permit removable insertion of a suitable inoculation syringe 27 into the biomedia growth chamber in a manner which permits introduction of the desired inoculation media. An ingress mechanism such as an inoculation septum can also be used for the removable egress of other mechanical devices such as a probe or other sensor device which could be used to monitor biological function in the cellular media 12 or conditions in the environment surrounding the cellular media 12.

Introduction of inoculation compounds can also be accomplished from a suitable inoculation storage reservoir such as storage reservoir 18' which is in communication with a suitable electronically controllable jetting device 16' to permit introduction of discrete quantities of suitable inoculation media into the biomedia growth chamber 14. For purposes of this disclosure, the term "inoculation media" is defined as any compound or composition which may prompt a response in the cellular media 12. Such materials can include, but are not limited to, suspect or confirmed pathogen, mutagenic agents, recombinant biological material as well as the environmental and protein material mentioned previously.

The culture device 10 can also include a suitable effluent removal mechanism associated with the biomedia growth chamber 14. The effluent removal mechanism is capable of removing byproducts of biological function to maintain the environment in the biomedia growth chamber 14 in a balance suitable for maintaining and promoting biological function of the cellular media 12. The effluent removal mechanism can be a suitable microfluidic pump in communication with an appropriately configured storage chamber such as chamber 26 depicted in FIG. 3. The microfluidic pump can be a suitably configured electronically controllable jetting device such as jetting device 28 which communicates with a suitable orifice 30 to accomplish removal of effluent material.

It is contemplated that introduction of materials such as nutrients and other media and removal of effluent can be balanced to ensure an appropriate balance in the biomedia growth chamber 14. The operation of microfluidic pumps and/or other devices which make up the effluent removal mechanism can be synchronized with devices introducing material into the biomedia growth chamber 14 to maintain proper or desired fluid levels in the growth chamber 14.

The culture device 10 can also include at least one heating mechanism capable of regulating temperature in the closed biomedia growth environment. As depicted in FIG. 3, temperature regulation may be accomplished by the activation of various resistors 32 which are a part of the associated electronically controllable jetting devices 16, 16'. Resistor 32 may accomplish either direct heating of the environment or heat the environment indirectly by elevating the temperature of the material introduced through the various electronically controllable jetting devices 16, 16'.

While the cellular media 12 set forth in FIG. 3 is depicted as a plurality of cells, it is understood that the device 10 may include any suitable cellular material capable of maintaining or performing a functionality of a chemical or biological nature and being contained within the biomedia growth chamber 14. It is contemplated that such material can be introduced into the biomedia growth chamber 14 during device assembly or can be introduced thereafter by any suitable means or mechanism. It is contemplated that the cellular material may be maintained in an inert state and activated upon receipt of suitable nutrient materials. Alternately, the cellular material may be maintained in a non-inert state depending upon the intended function and purpose of the culture device 10. Cellular material which can be integrated into the device of the present invention includes, but is not limited to, at least one of individual cells of a unitary homogeneous cell line, individual cells of multiple differentiated or nondifferentiated cell lines, individual identifiable subcellular structures including but not limited to viruses, retroviruses, prions, cellular organelles, and other material. Cellular organelles and material include but are not limited to mitochondria, Golgi bodies, various chloroblasts, endoplasmic reticulum, nuclear material such as the nucleolus, and the like.

Figure 4:
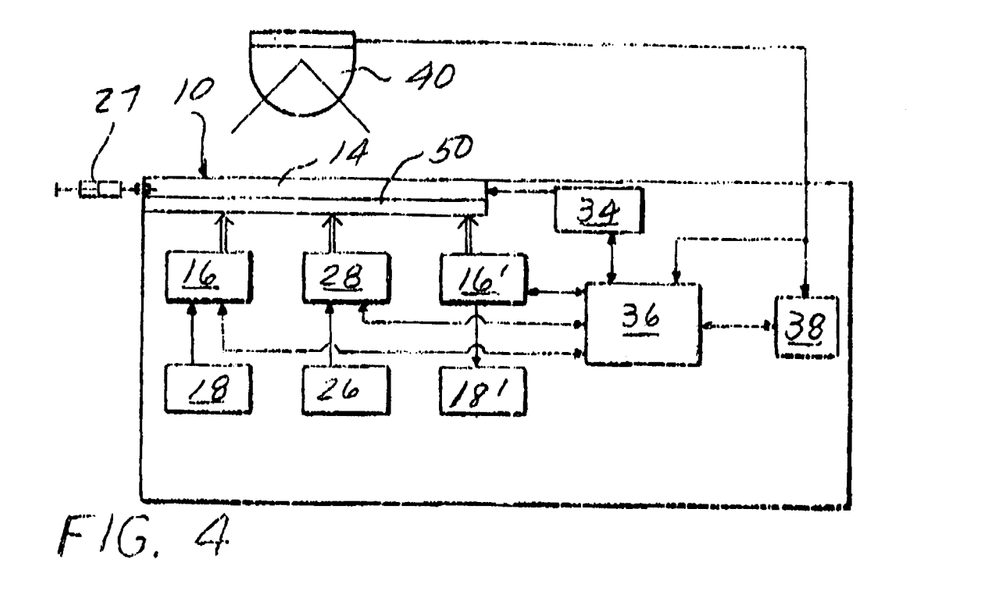
FIG. 4 is a schematic representation of the culture device of FIG. 3.

As depicted in FIG. 3 and schematically represented in FIG. 4, the culture device 10 disclosed can also include at least one suitable monitoring and sensor device 34 associated with the biomedia growth chamber 14. The sensor device(s) 34 can be capable of monitoring a function or function occurring on or in an individual cell or cells either directly or by inference. The sensor device 34 may also be capable of monitoring at least one important factor pertaining to the environment of the biomedia growth chamber 14. Examples of the such factors include, but are not limited to, temperature, environmental pH, air quality or composition and the like. Observation and analysis of factors involving the environment of the biomedia growth chamber 14 can provide information regarding general health and function of the biomedia growth chamber 14. It is understood that such information can also be used to infer information regarding the health and/or function of cellular material in the biomedia growth chamber 14. Sensor device 34 will have suitable capability to obtain data and transmit the data to appropriate controller 36 depicted in FIG. 4 to regulate and/or record the conditions within the biomedia growth chamber 14.

The actuation of electronically controllable jetting devices 16, 16' can be governed by suitable control mechanisms such as appropriately configured control electronics which are associated with the cell culture device 10 and are placed in electronic communication with the various jetting devices 16, 16'. As disclosed herein actuation of the electronically controllable jetting devices 16, 16' is governed by control electronics 36. Control electronics 36 can be maintained in or on any suitable location. As depicted in FIG. 2, control electronics 36 are depicted integrated into the substrate 50 of cell culture device 10. Control electronics 36 are also schematically depicted in FIG. 4. Control electronics 36 employed in or with the cell culture device 10 disclosed are capable of generating at least one command which is actionable on an electronically controllable jetting device 16, 16' and/or the effluent removal mechanism 28.

In the cell culture device 10 as disclosed, the control electronics 36 can also have capability of receiving external input and/or providing data or signals external to the device. This is depicted schematically as interface 38. As disclosed, interface 38 may be in electronic communication with a suitable investigational or monitoring device such as investigational device 40.

Figure 5:
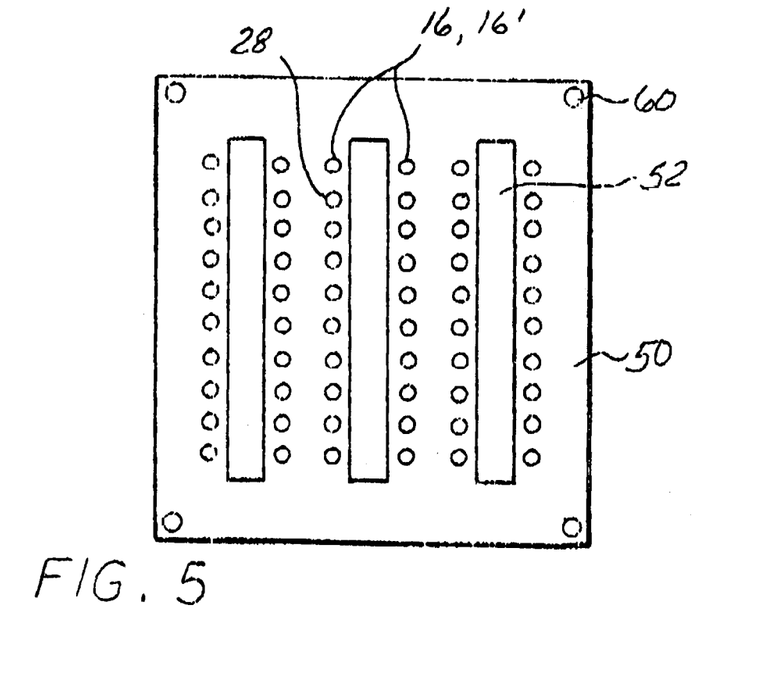
FIG. 5 is a top view of the substrate portion of the culture device of FIG. 2.

As best illustrated in FIGS. 2 and 3, the culture device 10 can include a substrate 50 having a slot 52 defined therein. It is contemplated that slot 52 can communicate with a chamber or chambers to provide continuous access to materials contained therein in situations where such unregulated access is desired or required. As best seen in FIG. 5, plurality of electronically controllable jelling devices 16, 16' can be defined in or associated with the substrate 50. Each electronically controllable jelling device 16, 16' communicates with an appropriate storage reservoir(s) 18, 18' to deliver material into the biomedia growth chamber 14 or remove components therefrom. It is contemplated that slot 52 can provide for continuous addition of materials such as nutrients and the like having non-critical dosage amounts. Electronically controllable jetting devices such as 16, 16' and 28 can be employed to dispense and/or remove discrete quantities of material into the biomedia growth chamber 14.

As best seen in FIG. 3, housing 54 is in overlying relationship with the substrate 50 to define the biomedia growth chamber 14. The housing 54 can include at least one region which facilitates observation of cellular material contained in the culture chamber. It is envisioned that the housing 54 may be transparent or include regions of transparency which will permit observation by various investigational devices 40 which can include, but are not limited to visual enhancement devices such as microscopes, scanning electron microscopes and the like. It is also contemplated that the investigational device 40 can be on of many devices such as infrared scanners, electrofluorescence detecting devices and the like. Furthermore, it is also contemplated that regions of the housing 54 can be configured to transmit data such as changes in cell temperature or the like as would be feasible and appropriate. Other methods of observation and analysis are to be considered within the purview of this invention. Thus, a housing material which facilitates such observation is considered within the purview of this invention.

The housing 54 may also include access portals and the like. These include the access septum associated with syringe 27 illustrated in FIG. 3 as well as access portals which communicate with the external environment in a manner appropriate with the end use function of the device 10. Other portals, orifices and the like can be positioned in the housing 54 to permit and/or regulate interaction with surrounding environment in the event that such interaction is required by the test protocol in which the cell culture device 10 is employed. One such non-limiting example of this is worker exposure monitoring or testing for a given toxic substance of substance panel existing in the surrounding environment. In such situations, it is contemplated that the housing 54 of the cell culture device 10 can be configured with suitable access orifices to permit entry of material from the surrounding environment into the biomedia growth chamber 14.

The culture device 10 can be configured and dimensioned such that slot 52 and orifices 20, 20' associated with electronically controllable jetting devices 16, 16' are configured and sized to prevent ingress of the cellular media under study. Thus, it is contemplated that the biomedia support region 22 will be sized to maintain biological and/or chemical function for between 1 and 10,000 cells. It is also contemplated that slot 52 as well as orifice 20, 20' will be of a size small enough to prevent ingress of material from the biomedia growth chamber 14.

Biomedia ingress into regions such as slot 52 and orifices 20, 20' associated with electronically controllable jetting devices 16, 16' can also be deferred by suitable mechanical or chemical-mechanical devices. These can include, but are not limited to, nozzle and slot geometries and the interposition of water insoluble thin film membrane over nozzle orifices which will permit the passage of ejected droplets but prevent ingress of biomedia material.

The biomedia growth chamber 14 can be configured to include a plurality of sub-chambers. It is contemplated that each subchamber will be served by appropriate electronically controllable jetting device(s) and slot(s) to provide nutrients, inoculants and various other materials desired or required in the given subchamber. It is contemplated that the cell culture device 10 as disclosed can have multiple subchambers with the various subchambers served by appropriate electronic jetting devices and slot(s). The multiple subchambers are oriented perpendicularly to the slots and provide a device whereby different testing conditions or variations can be performed in a single culture device.

Housing 54 can be configured to partition the biomedia growth chamber 14 into a plurality of discrete and isolated sub-chambers. Each sub-chamber can be configured to contain a specified number of cells or amount of biomaterial. The individual sub-chambers can be isolated from interaction with one another or can be configured to permit limited and/or controlled interaction depending on the nature of the cellular material or studies conducted. It is contemplated that the dividers 58 can be positioned in the biomedia growth chamber 14 to define the sub-chambers. As depicted in FIG. 2, dividers 58 can be contiguously joined to internal surfaces of the housing 54 and run perpendicularly to the slots 52 to defined the desired sub-chambers. Thus, each sub-chamber will be served by a series of nozzle members associated with a jetting device 16, 16' in communication with an associated storage reservoir 18, 18' as well as effluent removal devices where appropriate. In this way, nutrients, inoculants and various materials can be introduced and removed from each sub-chamber. It is contemplated that the configuration of sub-chambers can be employed to culture a variety of different cell lines in various sub-chambers to study and determine various dose responses. It is also contemplated that the various sub-chambers can hold identical or similar cell lines to which various inoculants am introduced in various exposure regimens to determine differences in response.

Housing 54 can be affixed to the substrate 50 by any suitable mechanism which will provide appropriate isolation from the surrounding environment as required or desired. As depicted in FIG. 3, a suitable seal 56 is positioned between substrate 50 and housing 54. Additionally, housing 54 and substrate 50 can include appropriate locators such as locators 60 or position grooves (not shown) to securely affix and position the housing 54 with respect to the substrate 50.

While the culture device 10 as disclosed includes two storage reservoirs 18, 18' and effluent storage reservoir 26, it is contemplated that any number of material sources and associated reservoirs can be employed. Thus, the culture device 10 of the present invention can include dedicated jetting devices for introducing various nutrients, additives and the like. It is also contemplated that the nutrients and/or inoculants can be stored in different storage reservoirs in a manner which will permit varying ratios of materials to be introduced into the culture device 10.

As shown in FIG. 1, the culture device 10 as disclosed can be integrated into a suitable cartridge 11. Where desired, the cartridge 11 is composed of a housing 46 which is configured to contain various materials employed in maintaining biological function in reservoirs defined therein. The culture device 10 can also include suitable electrical and/or electronic interfaces 48 that communicate with external devices to receive information and/or convey information regarding the materials contained in the cartridge 11, as well as particulars regarding the culture device 10 and contents thereof.

It is also contemplated that the culture device 10 can incorporate cellular media as cell-based sensing systems or cytosensors. As used herein, the term "cytosensor" is defined as a system having a biological/electronic interface. The biological component is capable of generating a biological response to a stimulus. The electronic component is capable of detecting the response and transmitting a signal based thereon. The stimulus detected can be any number of things such as exposure to a compound or composition. The biological response may be any of a number of response mechanisms including but not limited to alteration in cell membrane characteristics, changes in protein synthesis, changes in various metabolic functions and the like.

Cell-based biosensors or cytosensors can include, but are not limited to, devices employed in a variety of applications such as olfactory detection devices such as the electronic nose, emerging disease state monitoring and toxin build-up protection. Such systems can utilize a variety of precise cell lines as sensor elements. The cell type employed can be one which is well suited to the non-specific detection of biological agents. One example of a type of desirable cell line for use in cytosensor systems would be a cell line that can function as a non-conformal biological toxicity-sensing element for a wide variety of agents. One such non-limiting example of such a cell line would be chromatophore-type cells such as betta Splendens. Such cells typically exhibit cell responses which occur as a consequence of signals from peripheral nerves and through various circulating hormones. The signals are mediated by specific receptors at the cell surfaces and involve microtubule-associated movement of pigment particles. Integration of the cell line into the culture device 10 will permit maintenance of cell health and performance for extended periods of time. Survival and function of primary tissue isolates from various cell lines can exhibit extended viability.

Cell lines such as chromatophores can be integrated into cytosensor configurations within the biomedia growth chamber 14 of the cell culture device 10 disclosed herein to permit detection or study of a wide variety of materials including but not limited to neurotransmitters, adrenergic antagonists, serotonergic antagonists, hormones, cytoskeletal inhibitors, signal transduction modulators, membrane voltage modulators, neurotoxins, protein kinase modulators, polycyclic and aromatic hydrocarbons, phychogenic agents, pathogenic bacteria, uncharacterized algal toxins, purified bacterial protein toxins, pathogenic bacteria, bacterial isolates, antibacterial agents, fungi, antifungal and antiprotozoal agents, and organophosphate nerve agents.

Figure 6:
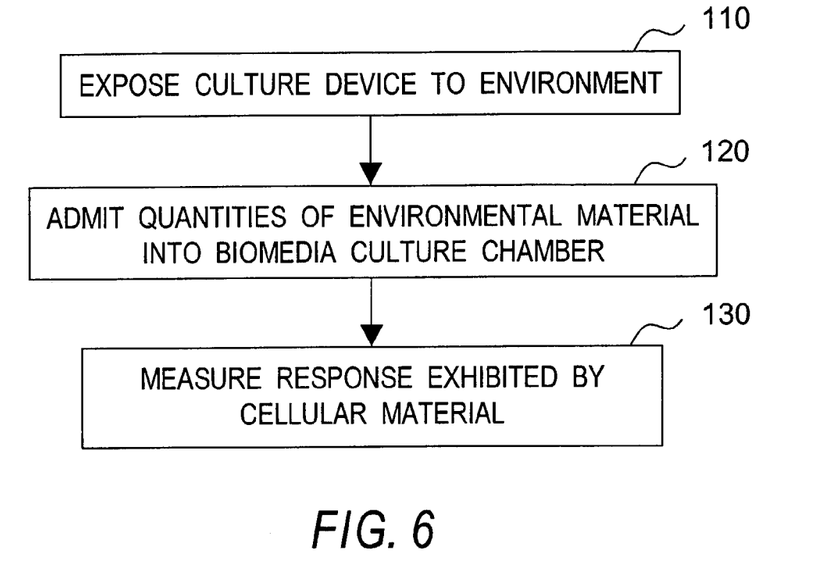
FIG. 6 is a process diagram of a monitoring a detection method employing the culture device of FIG. 2.

Referring now to FIG. 6, disclosed is a method for detecting a contaminant or pathogen in an external environment, in which the culture device 10 is exposed to the external environment according to a suitable exposure protocol as at reference numeral 110. Exposure can be accomplished by admitting appropriate quantities of environmental sample as at reference numeral 120. The response by the cellular material upon exposure to environmental material is measured at reference numeral 130. In implementing the detection method, an appropriate cytosensor can be employed in the cell culture device 10. While it is contemplated that the environment monitored can be composed of a gas or liquid which can be suitably monitored, it is envisioned that the method and device can be advantageously employed to detect and monitor exposure to various biotoxins in gaseous media. To further implement the detection method, it is contemplated that the ingress of contaminant media can be timed or controlled to provide appropriate monitoring and detection. Control can include removal of seals to permit or initiate ingress. Control can also regulate the size of any ingress orifices to control cytosensor exposure to remain within detection limits for optimum function and operation according to appropriate operational protocols and regimens.

The method can be implemented by employing the cell culture device 10 disclosed herein in a suitably configured detection device. Suitable detection devices can be employed to detect biological pathogens; such devices may broadly include a cytosensor and cytosensor response mechanism. The cytosensor is maintained in a growth chamber which has electronically controllable jetting device(s) communicating therewith. The jetting device conveys quantities of compounds into the growth chamber. The sensor device can include an inlet in communication with the cytosensor growth chamber that is capable of conveying environmental material into communication with the cytosensor. Suitable cytosensors are biological isolates which exhibit sensitivity to at least one of nerve agents, pathogenic bacteria, protein toxins, neurotoxins, bacteria toxins, and fungal resins.

Figure 7:
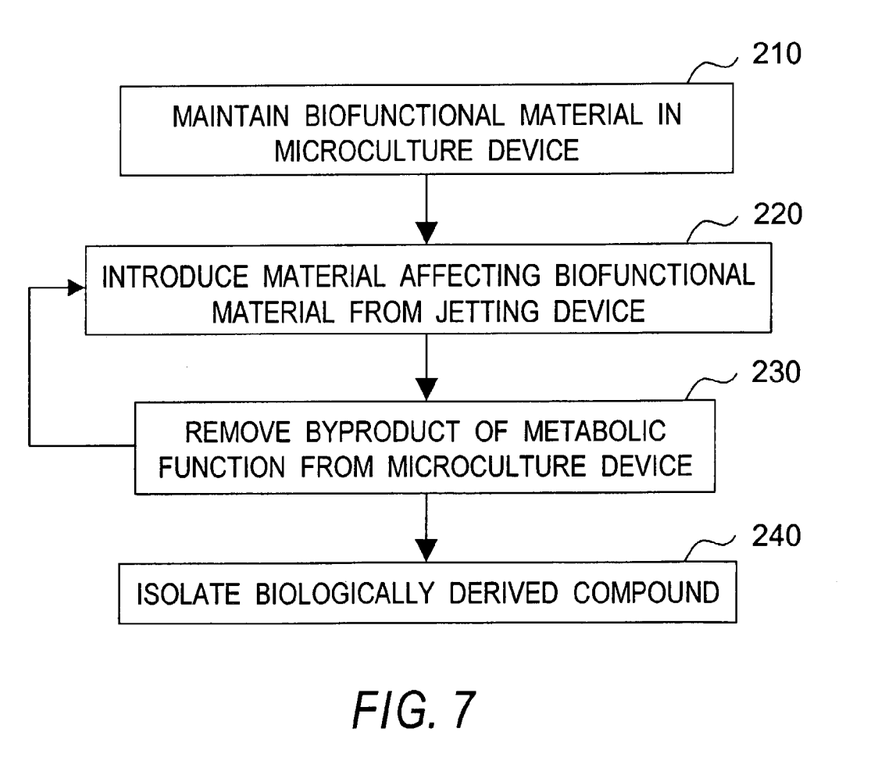
FIG. 7 is a process diagram of a synthesis method utilizing the culture device of FIG. 2.

Also disclosed and illustrated in FIG. 7 is a method for producing biologically derived compounds in which biofunctional material is maintained in a growth chamber associated with a microculture device such as cell culture device 10 at reference numeral 210. At least one byproduct of metabolic function of the biofunctional material is removed from the growth chamber at reference numeral 230. The removed byproduct of metabolic function contains the biologically derived compound which can be collected and processed as desired or required at reference numeral 240. The method disclosed also contemplates the step of introducing an additional compound into contact with the biofunctional material which is capable of affecting function of the biofunctional material as depicted at reference numeral 220. Suitable material which can affect biofunction can include, but is not limited to genetic alteration material, challenge microbes, antigens, and the like which will stimulate production of the desired biological material. Suitable biological materials can include, but are not limited to, various proteins, hormones, immunological materials and the like.

While the invention has been described in connection with what is presently considered to be the most practical and preferred embodiment, it is to be understood that the invention is not limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as permitted under the law.

What is claimed is:

1. A culture device for cellular media, comprising:
   a housing in overlying relationship with a substrate, thereby defining a closed environment biomedia growth chamber;
   a biomedia support surface integrally formed with the housing within the closed environment biomedia growth chamber;
   a source of material supporting cellular function; and
   an electronically controllable jetting device in communication with the source of material supporting cellular function, the jetting device emitting the material into the biomedia growth chamber, wherein the jetting device is at least one of a thermal ink jet device or a piezo-electric ink jet device.

2. The culture device of claim 1, further comprising a storage reservoir in communication with the electronically controllable jetting device.

3. The culture device of claim 1 wherein the electronically controllable jetting device has an orifice outlet in communication with the biomedia growth chamber.

4. The culture device of claim 3 wherein the biomedia growth chamber is positioned to overlay the orifice outlet defined in the electronically controllable jetting device.

5. The culture device of claim 1 wherein the biomedia support surface is positioned relative to the jetting device at a location capable of facilitating observation and analysis of cellular function.

6. A culture device for cellular media, comprising:
   a biomedia growth chamber defining a closed environment;
   a source of material supporting cellular function;
   an electronically controllable jetting device in communication with the source of material supporting cellular function, the jetting device emitting the material into the biomedia growth chamber, wherein the jetting device is at least one of a thermal ink jet device or a piezo-electric ink jet device; and
   an inoculation septum defined in the biomedia growth chamber, the inoculation septum providing closed communication between the biomedia growth chamber and an environment external to the biomedia growth chamber.

7. A culture device for cellular media, comprising:
   a biomedia growth chamber defining a closed environment;
   a source of material supporting cellular function; and
   an electronically controllable jetting device in communication with the source of material supporting cellular function, the jetting device emitting the material into the biomedia growth chamber, wherein the jetting device is at least one of a thermal ink jet device or a piezo-electric ink jet device;
   wherein the biomedia growth chamber overlays multiple orifice outlets.

8. The culture device of claim 2 wherein the storage reservoir contains compounds appropriate to maintain stable biomedia growth in the biomedia growth chamber.

9. The culture device of claim 2, further comprising an effluent removal mechanism associated with the biomedia growth chamber.

10. The culture device of claim 9 wherein the effluent removal mechanism is a microfluidic pump.

11. The culture device of claim 10 wherein the microfluidic pump is in communication with the storage reservoir.

12. The culture device of claim 1, further comprising a temperature regulating mechanism capable of controlling temperature in the biomedia growth chamber.

13. The culture device of claim 1, further comprising cellular material capable of one of maintaining and performing a functionality of one of a chemical and a biological nature, the cellular material contained in the biomedia growth chamber.

14. The culture device of claim 13 wherein the cellular material is selected from individual cells, cellular organelles, individual identifiable subcellular structure, and combinations thereof.

15. The culture device of claim 1, further comprising a sensor associated with the biomedia growth chamber, the sensor capable of monitoring a condition selected from temperature, cellular respiration, pH occurring in the closed environment, and combinations thereof.

16. A culture device for cellular media, comprising:
    a biomedia growth chamber defining a closed environment;
    a source of material supporting cellular function;
    an electronically controllable jetting device in communication with the source of material supporting cellular function, the jetting device emitting the material into the biomedia growth chamber, wherein the jetting device is at least one of a thermal ink jet device or a piezo-electric ink jet device; and a substrate, the substrate having a slot defined therein, wherein the electronically controllable jetting device is associated with the slot.

17. The culture device of claim 16, further comprising a housing in overlying relationship with the substrate, the housing defining the biomedia growth chamber.

18. The culture device of claim 17 wherein the housing includes at least one region which facilitates observation of a cellular material contained in the biomedia growth chamber.

19. The culture device of claim 17 wherein the housing includes at least one access septum.

20. The culture device of claim 17 wherein the biomedia growth chamber is configured to contain between one and ten thousand cells.

21. The culture device of claim 17 wherein the housing includes at least one divider oriented essentially perpendicular to the slot defined in the substrate, the divider defining distinct subchambers in the biomedia growth chamber.

22. The culture device of claim 1, further comprising a controller electronically actionable on the jetting device to regulate emission of the material into the biomedia growth chamber.

23. A culture device for cellular media, comprising:
a biomedia growth chamber defining a closed environment;
a plurality of reservoirs, each reservoir containing a material which affects cellular function;
a controller; and
a plurality of electronically controllable jetting devices, wherein each electronically controllable jetting device is in communication with one of the plurality of reservoirs, wherein the jetting devices emit the material into the biomedia growth chamber in response to a signal emitted by the controller, and wherein each of the plurality of jetting devices is at least one of a thermal ink jet device or a piezo-electric ink jet device.

24. The culture device of claim 23 wherein the signal emitted by the controller is governed by at least one of a preprogrammed regimen or function sensed in the biomedia growth chamber.

25. The culture device of claim 23, further comprising an effluent removal mechanism in communication with the biomedia growth chamber.

26. The culture device of claim 25 wherein the effluent removal mechanism is a microfluidic pump.

27. The culture device of claim 26 wherein the microfluidic pump is in fluid communication with an effluent collection reservoir.

28. The culture device of claim 23 wherein each of the plurality of jetting devices has an orifice outlet in communication with the biomedia growth chamber.

29. The culture device of claim 28 wherein the biomedia growth chamber is positioned to overlay the orifice outlets defined in the jetting devices.

30. The culture device of claim 23 wherein at least one of the plurality of reservoirs contains a biocidal agent.

31. The culture device of claim 23, further comprising a temperature regulating mechanism capable of controlling temperature in the biomedia growth chamber.

32. The culture device of claim 23, further comprising biofunctional material capable of performing a process which includes a functionality selected from a biological nature, a chemical nature, an electrochemical nature, and combinations thereof, the biofunctional material contained in the biomedia growth chamber.

33. The culture device at claim 32 wherein the biofunctional material is selected from homogeneous individual cells, mixed individual cells, cellular organelles, subcellular material, and combinations thereof.

34. The culture device of claim 33 wherein the subcellular material is selected from viruses, retroviruses, prions, and combinations thereof.

35. The culture device of claim 33 wherein the cellular organelles are selected from mitochondria, Golgi bodies, endoplasmic reticulum, chloroplasts, and combinations thereof.

36. The culture device of claim 23, further comprising a sensor associated with the biomedia growth chamber, the sensor capable of monitoring a condition selected from temperature, cellular respiration, pH occurring in the closed environment, and combinations thereof.

37. A culture device for cellular media, comprising:
a substrate having a slot defined therein;
a housing overlying the substrate, the housing having at least one central chamber defined therein; and
an electronically controllable jetting device associated with the slot defined in the substrate, the jetting device in communication with a source of a material which affects cellular function to be introduced into the central chamber, wherein the jetting device is at least one of a thermal ink jet device or a piezo-electric ink jet device.

38. The culture device of claim 37 wherein the substrate is composed of a material which is electronically compatible and is essentially non-interactive with cellular material.

39. The culture device of claim 37 wherein the substrate is silicon.

40. The culture device of claim 37, further comprising a storage chamber in fluid communication with the jetting device.

41. The culture device of claim 40 wherein the storage chamber contains nutrients capable of supporting metabolic activity of cellular media.

42. The culture device of claim 37, further comprising a biomedia support structure contained within the central chamber, the biomedia support structure positioned proximate to the jetting device.

43. The culture device of claim 37, further comprising cellular material, the cellular material capable of performing a function selected from a chemical function, a biological function, and combinations thereof.

44. The culture device of claim 37, further comprising a sensor associated with the central chamber, the sensor capable of monitoring a condition selected from temperature, cellular respiration, pH occurring in the central chamber, and combinations thereof.

45. The culture device of claim 37, further comprising an effluent removal mechanism, the effluent removal mechanism associated with the central chamber and in communication with a storage chamber.

46. The culture device of claim 45 wherein the effluent removal mechanism is a microfluidic pump.

47. The culture device of claim 46 wherein the microfluidic pump is in communication with the storage chamber.

48. A method of producing a biologically derived compound, comprising the steps of:
maintaining cellular material in a growth chamber associated with a microculture device, the microculture device including a biomedia growth chamber and at least one of a thermal ink jet device or a piezo-electric ink jet device; and removing a byproduct of metabolic function of the cellular material, the byproduct of metabolic function containing the biologically derived compound.

49. The method of claim 48, further comprising the step of introducing a compound into contact with the cellular material, the compound capable of affecting function of the cellular material.

50. The method of claim 49 wherein the introduced compound is brought into contact with the cellular material through the jetting device.

51. The method of claim 48 wherein the cellular material is selected from individual cells, subcellular material, and combinations thereof.

52. The method of claim 48, further comprising the step of altering at least one condition in the growth chamber.

53. The method of claim 52 wherein the at least one condition is selected from temperature, system pH, nutrient supply, nutrient composition, and combinations thereof.

54. A device for monitoring a cellular response mechanism, the device comprising:
a substrate having a slot defined therein;
a housing overlying the substrate, the housing defining a biomedia growth chamber;
an electronically controllable jetting device in communication with a source of material to be introduced into the biomedia growth chamber, wherein the jetting device is at least one of a thermal ink jet device or a piezo-electric ink jet device; and
cellular material located in the biomedia growth chamber, the cellular material generating a response mechanism in reaction to a stimulus.

55. The device of claim 54 wherein the substrate is composed of a material which is non-reactive to the cellular material contained in the biomedia growth chamber.

56. The device of claim 55, further comprising a reservoir containing the material to be introduced into the biomedia growth chamber, wherein the reservoir is in communication with the jetting device.

57. The device of claim 56, further comprising a support surface for positioning the cellular material, the support surface positioned in the biomedia growth chamber at a location proximate to the jetting device.

58. The culture device of claim 57 wherein the support surface is positioned relative to the jetting device at a location capable of facilitating observation and analysis.

59. The culture device of claim 57 wherein the support surface is configured to maintain a discrete, finite quantity of individual cells.

60. The culture device of claim 54, further comprising at least one device associated with the biomedia growth chamber, the device capable of monitoring a function occurring in or on the cellular material.

61. The culture device of claim 54 wherein the housing includes an ingress orifice establishing communication with an environment external to the biomedia growth chamber.

62. A method for detecting a contaminant in an external environment, the method comprising;
exposing a culture device to the external environment according to an exposure protocol, wherein the culture device includes, a biomedia growth chamber defining a closed environment, cellular material contained in the biomedia growth chamber, and an electronically controllable jetting device in communication with a source of material supporting cellular function, wherein the jetting device is at least one of a thermal ink jet device or a piezo-electric ink jet device;
admitting environmental material into the biomedia growth chamber; and
measuring response exhibited by the cellular material upon exposure to environmental material.

63. The method of claim 62 wherein the external environment is gaseous.

64. The method of claim 62 wherein the cellular material is selected from single cells, subcellular material, and combinations thereof, the cellular material exhibiting a response upon contact with a compound contained in the external environment.

65. The method of claim 62, further comprising the step of controlling ingress of external environmental material to the biomedia growth chamber.

66. A cartridge, comprising:
a housing in overlying relationship with a substrate, thereby defining a closed environment biomedia growth chamber;
a biomedia support surface integrally formed with the housing within the closed environment biomedia growth chamber;
a source of material supporting biological function of a material contained in the biomedia growth chamber; and
an electronically controllable jetting device emitting the material supporting biological function into the biomedia growth chamber, wherein the jetting device is at least one of a thermal ink jet device or a piezo-electric ink jet device.

67. The cartridge of claim 66, further comprising cellular material contained in the biomedia growth chamber, the cellular material selected from individual cells, subcellular organelles, and combinations thereof.

68. The cartridge of claim 67, further comprising a reservoir for collecting effluent generated as a result of biological function of the cellular material.

69. The cartridge of claim 68, further comprising an effluent removal mechanism in communication with the biomedia growth chamber.

70. A sensor device for detecting biological pathogens, comprising;
a cytosensor;
a cytosensor response mechanism;
a housing in overlying relationship with a substrate, thereby defining a closed environment growth chamber that supports the cytosensor;
a biomedia support surface integrally formed with the housing within the closed environment growth chamber; and
an electronically controllable jetting device in communication with the growth chamber, the jetting device conveying quantities of a compound appropriate for cytosensor function into contact with the cytosensor, wherein the jetting device is at least one of a thermal ink jet device or a piezo-electric ink jet device.

71. The sensor device of claim 70, further comprising an inlet mechanism in communication with the cytosensor growth chamber, the inlet mechanism capable of conveying environmental material into communication with the cytosensor.

72. A sensor device for detecting biological pathogens, comprising:
a cytosensor;
a cytosensor response mechanism;

a growth chamber supporting the cytosensor, the growth chamber defining a closed environment; and an electronically controllable jetting device in communication with the growth chamber, the jetting device conveying quantities of a compound appropriate for cytosensor function into contact with the cytosensor, wherein the jetting device is at least one of a thermal ink jet device or a piezo-electric ink jet device;

wherein the cytosensor is a biological isolate which exhibits sensitivity to at least one of nerve agents, pathogenic bacteria, protein toxins, neurotoxins, bacteria toxins, or fungal resins.

73. A culture device for cellular media, comprising:

a housing in overlying relationship with a substrate, thereby defining a closed environment biomedia growth chamber;

a biomedia support surface integrally formed with the housing within the closed environment biomedia growth chamber; and at least one of a thermal ink jet device or a piezo-electric ink jet device adapted to emit material supporting biological function of the cellular media into the biomedia growth chamber.

74. The culture device of claim 73, further comprising means for removing effluent of the cellular media from the biomedia growth chamber.

75. The culture device of claim 73, further comprising means for monitoring at least one function occurring in the biomedia growth chamber.

76. The culture device of claim 73 wherein the biomedia growth chamber contains biofunctional material selected from-individual cells, cellular organelles, individual identifiable subcellular structure, and combinations thereof.

77. A culture device for cellular media, comprising:

a biomedia growth chamber defining a closed environment; and at least one of a thermal ink jet device or a piezo-electric ink jet device adapted to emit material supporting biological function of the cellular media into the biomedia growth chamber;

wherein the biomedia growth chamber contains biofunctional material selected from-individual cells, cellular organelles, individual identifiable subcellular structure, and combinations thereof;

and wherein the biomedia growth chamber includes at least two subchambers.

78. The culture device of claim 73, further comprising means for providing controlled access between the biomedia growth chamber and sources external thereto.

* * * * *

UNITED STATES PATENT AND TRADEMARK OFFICE
CERTIFICATE OF CORRECTION

PATENT NO.         : 7,141,386 B2                              Page 1 of 1
APPLICATION NO.    : 10/285800
DATED              : November 28, 2006
INVENTOR(S)        : John Stephen Dunfield et al.

It is certified that error appears in the above-identified patent and that said Letters Patent is hereby corrected as shown below:

On the face page, in field (75), in "Inventors", in column 1, line 2, delete "Ronni" and insert -- Ronnie --, therefor.

In column 3, line 10, delete "jelling" and insert -- jetting --, therefor.

In column 5, line 59, delete "jelling" and insert -- jetting --, therefor.

In column 5, line 61, delete "jelling" and insert -- jetting --, therefor.

In column 7, line 26, delete "am" and insert -- are --, therefor.

In column 12, line 3, in Claim 33, delete "at" and insert -- of --, therefor.

Signed and Sealed this

Twenty-first Day of April, 2009

JOHN DOLL
*Acting Director of the United States Patent and Trademark Office*